(12) United States Patent
Matsumoto et al.

(10) Patent No.: US 8,162,825 B2
(45) Date of Patent: Apr. 24, 2012

(54) ENDOSCOPE

(75) Inventors: Jun Matsumoto, Hino (JP); Shigeharu Suzuki, Hachioji (JP)

(73) Assignee: Olympus Corporation (JP)

( * ) Notice: Subject to any disclaimer, the term of this patent is extended or adjusted under 35 U.S.C. 154(b) by 1287 days.

(21) Appl. No.: 11/816,345

(22) PCT Filed: Feb. 15, 2006

(86) PCT No.: PCT/JP2006/302653
§ 371 (c)(1),
(2), (4) Date: Aug. 15, 2007

(87) PCT Pub. No.: WO2006/088058
PCT Pub. Date: Aug. 24, 2006

(65) Prior Publication Data
US 2009/0030280 A1    Jan. 29, 2009

(30) Foreign Application Priority Data
Feb. 15, 2005    (JP) .................................. 2005-038016

(51) Int. Cl.
*A61B 1/06* (2006.01)
*A61B 1/00* (2006.01)
*A61B 1/04* (2006.01)
(52) U.S. Cl. ...................................... 600/182; 600/133
(58) Field of Classification Search .................. 600/130, 600/133, 139, 140, 182
See application file for complete search history.

(56) References Cited

U.S. PATENT DOCUMENTS

| 5,716,322 A * | 2/1998 | Hui et al. ....................... 600/133 |
| 5,876,331 A * | 3/1999 | Wu et al. ....................... 600/139 |
| 6,923,757 B2 * | 8/2005 | Abe et al. ...................... 600/130 |
| 7,306,374 B2 * | 12/2007 | Hokkirigawa et al. ....... 384/297 |
| 2004/0028914 A1* | 2/2004 | Yanome ........................ 428/447 |
| 2004/0204540 A1* | 10/2004 | Shinozaki ..................... 524/588 |
| 2005/0020881 A1* | 1/2005 | Hosoi et al. .................. 600/140 |
| 2005/0020882 A1* | 1/2005 | Hosoi et al. .................. 600/140 |
| 2005/0061381 A1* | 3/2005 | Hosoi et al. .................. 138/137 |
| 2005/0148570 A1* | 7/2005 | Huang et al. ................. 514/192 |
| 2006/0058583 A1* | 3/2006 | Matsumoto et al. .......... 600/153 |

FOREIGN PATENT DOCUMENTS

| JP | 10-101453 | 4/1998 |
| JP | 2000-296413 | 10/2000 |
| JP | 2004-60773 | 2/2004 |
| JP | 2004-73259 | 3/2004 |
| JP | 2004-137371 | 5/2004 |
| JP | 2004-329539 | 11/2004 |

(Continued)

OTHER PUBLICATIONS

Untranslated Office Action issued by Japanese Patent Office on May 25, 2010 in connection with corresponding Japanese application No. 2007-503682.

(Continued)

*Primary Examiner* — Philip R Smith
*Assistant Examiner* — William Chou
(74) *Attorney, Agent, or Firm* — Ostrolenk Faber LLP

(57) ABSTRACT

An endoscope which includes a flexible tube and a protective tube placed in the flexible tube, the protective tube containing a plurality of elongated built-in components including an optical fiber bundle, characterized in that a solid lubricant containing rice-bran ceramics is interposed at interstices between the optical fibers placed in the protective tube and between the protective tube and the flexible tube.

6 Claims, 2 Drawing Sheets

FOREIGN PATENT DOCUMENTS

JP    2006-81749    3/2006

OTHER PUBLICATIONS

English translation of Japanese Office Action issued May 25, 2010 in connection with corresponding Japanese application 2007-503682.

PCT International Search Report and Written Opinion dated May 16, 2006 issued in corresponding PCT Application No. PCT/JP2006/302653.

PCT Notification of Transmittal of Translation of International Preliminary Report on Patentability in corresponding PCT Application No. PCT/JP2006/302653.

\* cited by examiner

ENDOSCOPE

CROSS REFERENCE TO RELATED APPLICATION

The present application is a 35 U.S.C. §§371 national phase conversion of PCT/JP2006/302653, filed Feb. 15, 2006, which claims priority of Japanese Patent Application No. 2005-038016, filed Feb. 15, 2005, the disclosure of which has been incorporated herein by reference. The PCT International Application was published in the Japanese language.

TECHNICAL FIELD

This invention relates to an endoscope provided with a solid lubricant which is excellent in resistance to autoclave sterilization (high-pressure/high-temperature steam sterilization) as well as to peroxide-based sterilization and which can be easily treated.

BACKGROUND ART

The endoscope is generally designed so as to be inserted into a body cavity of human body in order to perform the observation, examination, diagnosis and treatment of the body cavity of human body. The endoscope is generally constituted by a flexible inserting tube which is designed to be inserted into a body cavity, and a manipulation portion which is provided at a proximal end portion of this flexible inserting tube for manipulating a distal end portion of this flexible inserting tube so as to enable this distal end portion to bend. Further, this endoscope is also provided with a light guide flexible tube which is extended from the manipulation portion and connected with a light source device and a control device.

The flexible inserting tube is constituted by a flexible tube portion which is excellent in flexibility enabling it to follow up with the curvature of body cavity as this flexible tube portion is inserted into a curved body cavity, and a curved portion which is contiguously provided at a distal end of this flexible tube portion and can be optionally bent through the manipulation thereof.

Incidentally, this flexible inserting tube is provided therein with various members such as a bending mechanism for bending the curved portion existing at a distal end portion of the inserting tube, a light guide for transmitting light from a light source to the distal end portion of the inserting tube, an image guide for transmitting an image of a subject to the manipulation portion, a tube for introducing forceps to be employed in performing, for example, the treatment and cellular examination, an air/liquid feeding tube for enabling the injection of a medical liquid, etc., these members being disposed to extend longitudinally as required.

When these flexible tube portion and curved portion are caused to bend, friction is caused to be generated among various members that have been built in these flexible tube portion and curved portion, resulting in the generation of pressure acting on these members. Therefore, with a view to minimize these friction and pressure, a lubricant is applied to the outer circumferential wall of each of these members.

In order to prevent the infection to a patient or an operator, it is indispensable to apply a disinfection or sterilization treatment to the flexible tube portion and the distal end portion, which have been inserted into a curved body cavity, after the use thereof. Therefore, according to the prior art, gas such as ethylene oxide gas (hereinafter referred to as EOG) or a liquid disinfectant has been employed for the sterilization.

However, since EOG is toxic in itself and hence presents the problem of residual toxicity, the aeration of the flexible inserting tube is required to be performed for removing EOG, thus raising a problem that it takes a long time for the sterilization treatment of the flexible inserting tube. Namely, there is a problem that the aforementioned gas sterilization is expensive in running cost.

On the other hand, the latter sterilization treatment using a liquid disinfectant is also accompanied with problems that it may not be possible to secure sufficient sterilization effects and that it involves complicated administration of the liquid disinfectant. Additionally, there is a problem of how to handle the waste liquor thereof, thus raising the problem of increase in cost for the waste disposal that is required for obviating the problem of environmental pollution that may be caused by the waste liquor.

Because of these reasons, it is now desired to apply the high-pressure/high-temperature steam sterilization that has been conventionally employed for the sterilization of medical instruments. This high-pressure/high-temperature steam sterilization is advantageous in various aspects that since water is employed for the sterilization, the problem of residual toxicity can be obviated, that it is possible to secure strong sterilizing effects, that the time required for the sterilization treatment is relatively short, that the running cost for the sterilization can be saved, and that there is no possibility of generating waste liquor.

However, in this high-pressure/high-temperature steam sterilization, steam is permitted to permeate through various materials of the components constituting the endoscope, such as rubber, macromolecular material such as plastics, adhesive, etc. Therefore, when the endoscope which is conventionally constructed into a water-tight structure is placed in a high-pressure/high-temperature steam sterilization apparatus and subjected to sterilization treatment, there may be raised a problem that the steam is permitted to permeate even into the interior of the endoscope that has been constructed into a water-tight structure by the ordinary method using an O-ring, an adhesive, etc.

Further, on the occasion of high-pressure/high-temperature steam sterilization, it has been generally practiced to place the endoscope in a high-pressure/high-temperature steam sterilization apparatus in such a manner that the interior of endoscope is kept communicated with the exterior thereof in order to prevent fracture of the sheath of the curved portion of endoscope. On this occasion, high-pressure/high-temperature steam is permitted to enter into the interior of endoscope, thus causing a light guide fiber bundle formed of a bundle of a large number of glass fibers to contact with this high-pressure/high-temperature steam, occasionally resulting in the damage to the light guide fiber bundle or in the damage to the lubricity thereof.

More specifically, in the case of the conventional endoscope, molybdenum disulfide is employed as a solid lubricant to be interposed between a protective tube for covering the light guide fiber bundle and a sheath tube. Therefore, when this molybdenum disulfide is caused to contact with the high-pressure/high-temperature steam, this molybdenum disulfide may be aggregated and adhered to these tubes or oxidative degradation of molybdenum disulfide may be caused to occur, thus causing the generation of sulfurous gas or the generation of cracks in the rubber sheath tube, occasionally resulting in the breakage of fibers.

Meanwhile, it is also desired to apply a peroxide-based sterilization method, e.g., a hydrogen peroxide low temperature plasma sterilization method to the endoscope. This hydrogen peroxide low temperature plasma sterilization method is advantageous in that it is not only possible to perform the sterilization treatment at normal temperature and under a low humidity but also possible to greatly minimize the generation of residual matters and secondary products after the sterilization, thus making it excellent in safety.

This hydrogen peroxide low temperature plasma sterilization method however is accompanied with a problem that free radicals such as hydroxyl radical, super-oxide, hydroxyperoxy radical, etc., are caused to be generated together with plasma in the sterilization apparatus, thereby permitting these free radicals to permeate through various materials of the components constituting the endoscope, such as rubber, macromolecular material such as plastics, adhesive, etc.

Furthermore, in the case of this hydrogen peroxide low temperature plasma sterilization method, for the purpose of more completely sterilize the interior of channel tube to be used for feeding air, a so-called booster which is formed of a vessel filled with a small amount of hydrogen peroxide is connected with the channel tube and this hydrogen peroxide is permitted to inject therefrom into the channel tube as a negative pressure is created therein. On this occasion however, this hydrogen peroxide is permitted to enter into the endoscope.

As in the case of the aforementioned high-pressure/high-temperature steam sterilization, these hydrogen peroxide and free radicals may become a cause for the oxidative degradation of molybdenum disulfide which is employed as a solid lubricant to be interposed between a protective tube and a sheath tube, thereby generating sulfurous gas or cracks in the sheath tube made of silicone rubber and disposed inside the protective tube, occasionally resulting in the breakage of fibers.

As described above, the sterilization treatments may become a cause for the denaturing or degradation of the lubricant, the degradation of lubricity or the breakdown of the endoscope.

The present invention has been made in view of overcoming the aforementioned problems and hence, the purpose of the present invention is to provide an endoscope which employs a solid lubricant which is capable of withstanding the sterilization treatments to be performed according to the high-pressure/high-temperature steam sterilization method or the hydrogen peroxide low temperature plasma sterilization method.

DISCLOSURE OF INVENTION

According to one aspect of the present invention, there is provided an endoscope comprising a flexible tube and a protective tube placed in the flexible tube, the protective tube containing a plurality of elongated built-in components including an optical fiber bundle, characterized in that a solid lubricant containing rice-bran ceramics is interposed at interstices between the optical fibers placed in the protective tube and between the protective tube and the flexible tube.

According to another aspect of the present invention, there is provided an endoscope comprising a flexible tube and a protective tube placed in the flexible tube, the protective tube containing a plurality of elongated built-in components including an optical fiber bundle, characterized in that a solid lubricant containing rice-bran ceramics, and carbon graphite and/or fluorinated resin is interposed at interstices between the optical fibers placed in the protective tube and between the protective tube and the flexible tube.

BEST MODE FOR CARRYING OUT THE INVENTION

Figure 1:
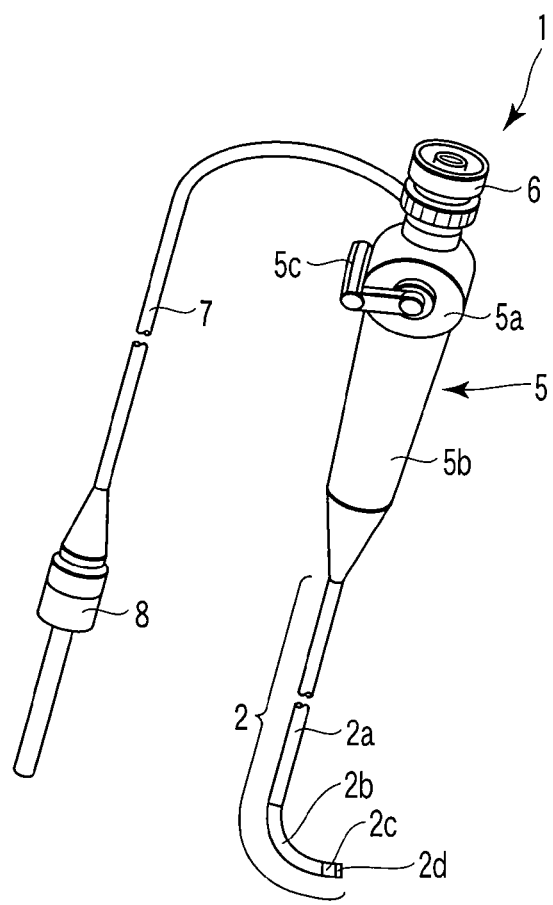
FIG. 1 is a perspective view illustrating entirely the construction of the endoscope according to one embodiment of the present invention.

Next, the best mode for carrying out the present invention will be explained.

The endoscope according to one aspect of the present invention is featured in that a solid lubricant containing rice-bran ceramics, or a solid lubricant containing rice-bran ceramics, and carbon graphite and/or fluorinated resin is interposed at interstices between the optical fibers placed in the protective tube and between the protective tube and the flexible tube.

In the case of the endoscope according to one aspect of the present invention which is constructed as described above, since a solid lubricant containing rice-bran ceramics, or a solid lubricant containing rice-bran ceramics, and carbon graphite and/or fluorinated resin is employed as a lubricant for preventing the damage of optical fibers such as a light guide or an image guide to be disposed in the flexible tube, the flexible tube is enabled to exhibit excellent resistance to the high-pressure/high-temperature steam sterilization as well as to the peroxide sterilization.

In the employment of the solid lubricant containing rice-bran ceramics, and carbon graphite and/or fluorinated resin, a mixing ratio of the carbon graphite and/or fluorinated resin to the rice-bran ceramics may preferably be confined to not more than 9 to 1. If the mixing ratio of rice-bran is lower than the aforementioned ratio, the lubricity of the solid lubricant may be degraded.

The solid lubricant to be used in one aspect of the present invention may be constructed such that the surface of particles of the solid lubricant is covered with an unsaturated ester monomer containing fluoroaliphatic group or with an unsaturated monosilane monomer. The solid lubricant constructed in this manner is advantageous in that the surface thereof is enabled to exhibit ultra-water repellency, that it exhibits especially excellent chemical stability to the high-pressure/high-temperature steam sterilization, and that, due to the ultra-water repellent surface thereof, the oxidative degradation of solid lubricant can be prevented even in the peroxide sterilization.

Further, the solid lubricant may preferably be selected from those which have an average particle diameter ranging from 0.1 to 150 μm. If the average particle diameter of the solid lubricant is less than 0.1 μm, the lubricity of the solid lubricant may be degraded. If the average particle diameter of the solid lubricant exceeds 150 μm, the assembling property thereof to the endoscope may be degraded. Incidentally, various kinds of solid lubricant differing in average particle diameter may be combined and employed as a mixture.

In this case, the rice-bran ceramics may be formed of a porous carbonaceous material which can be manufactured by a process comprising the steps of: adding a thermosetting resin and an appropriate quantity of an adhesive paste-containing aqueous solution or of water to brans such as rice bran and other grain bran to form a mixture and kneading the mixture; granulating the kneaded mixture containing the thermosetting resin and the brans to obtain granules having a predetermined grain size; filling a desired mold with the granules and molding the granules while applying pressure and deaeration to the granules to form a molded product; sintering the molded product released from the mold in an inert gas atmosphere or in a vacuum by increasing the temperature of the molded product up to an ultimate sintering temperature according to a predetermined rate of temperature increase to obtain a carbonized product; and cooling the carbonized product from the ultimate sintering temperature down to ordinary temperature according to a predetermined rate of temperature drop.

This porous carbonaceous material is excellent in heat resistance and cannot be oxidized even in a high-temperature/high-pressure steam atmosphere or in an atmosphere containing hydrogen peroxide or free radicals. Further, this porous carbonaceous material is also excellent in corrosion resistance and very excellent in adhesion to metals and glass.

As for the elongated built-in components having an optical fiber bundle placed in a protective tube, they include an image guide and a light guide.

According to one aspect of the present invention, since a solid lubricant containing rice-bran ceramics, or a solid lubricant containing rice-bran ceramics, and carbon graphite and/or fluorinated resin is employed, it is possible to minimize the bending resistance and to obtain an endoscope which is capable of minimizing the damage or fracture of optical fibers employed as a built-in member even if the endoscope is repeatedly used. Further, since a solid lubricant containing rice-bran ceramics, and a solid lubricant containing rice-bran ceramics, and carbon graphite and/or fluorinated resin are both excellent in resistance not only to the high-pressure/high-temperature steam sterilization but also to the hydrogen peroxide-based sterilization, it is possible to obtain an endoscope which is capable of withstanding repeated sterilization.

Figure 2:
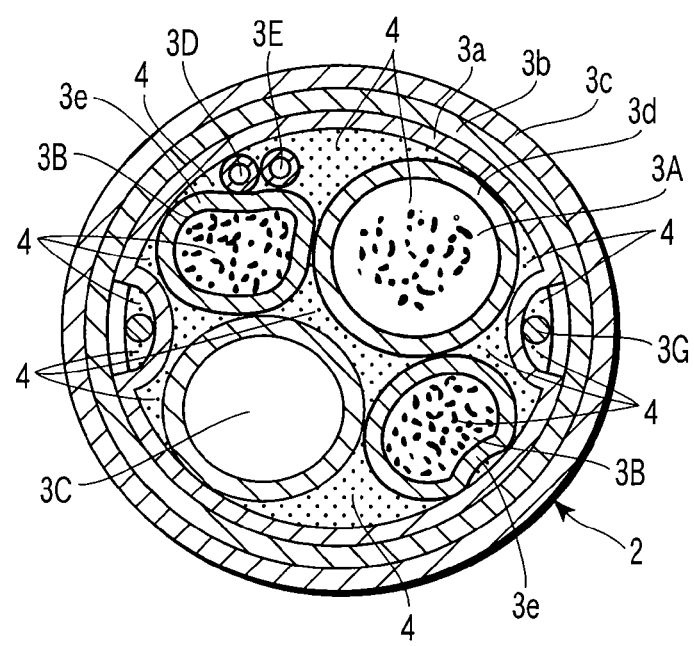
FIG. 2 is a cross-sectional view of the insertion portion of the endoscope shown in FIG. 1.
Figure 3:
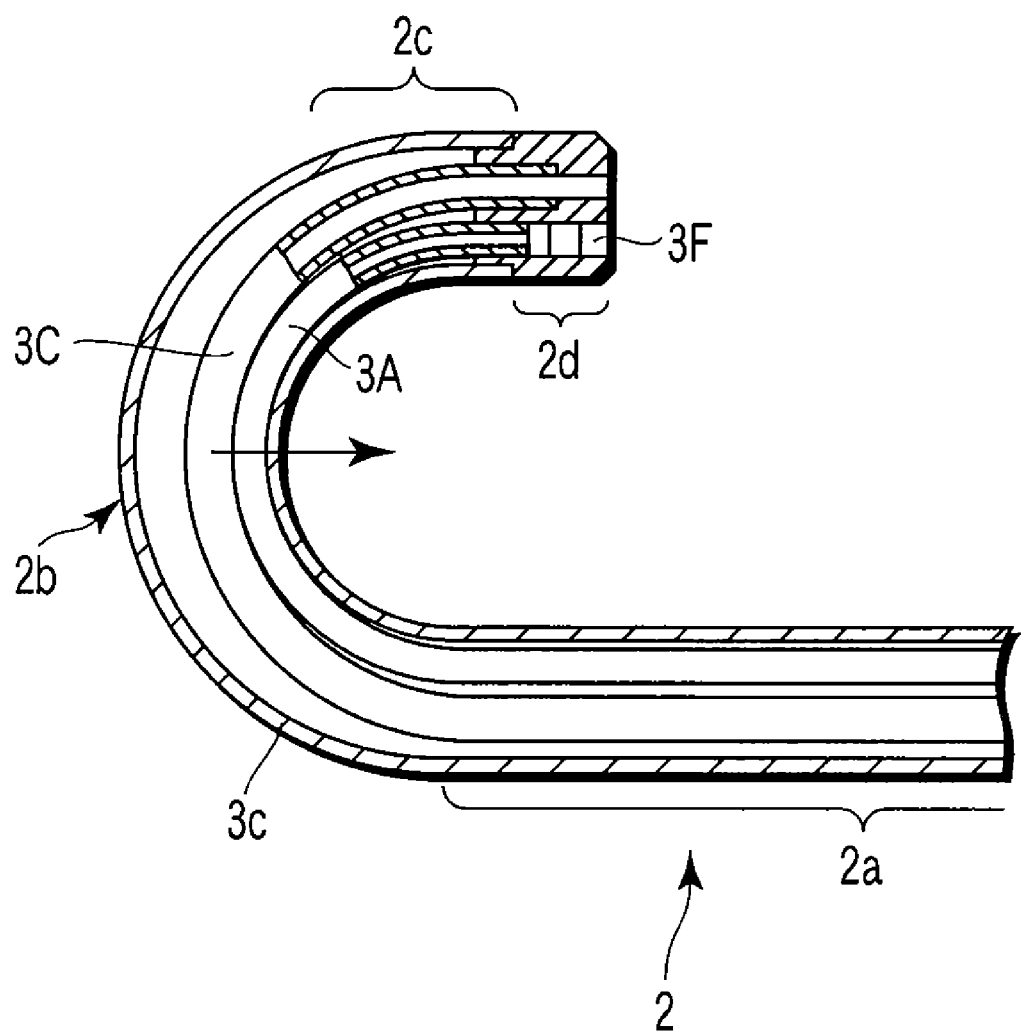
FIG. 3 is a longitudinal sectional view of the curved portion in the insertion portion of the endoscope shown in FIG. 1.

FIG. 1 shows the entire structure of a fiberscope type endoscope according to one embodiment of the present invention; FIG. 2 is a cross-sectional view of the flexible inserting tube of the endoscope shown in FIG. 1; and FIG. 3 is a longitudinal sectional view of the curved portion of the endoscope shown in FIG. 1. In the following description, an upper portion of the drawing shown in FIG. 1 will be referred to as "a proximal end portion" and a lower portion thereof will be referred to as "a distal end portion".

As shown in FIG. 1, the endoscope 1 according to one embodiment of the present invention comprises an elongated flexible inserting tube (flexible tube for endoscope) 2 which is excellent in flexibility (pliability), and a manipulation portion 5 which is provided at a proximal end portion of the flexible inserting tube 2.

The manipulation portion 5 is a portion which is grasped by an operator so as to manipulate the endoscope 1 entirely. As shown in FIG. 1, this manipulation portion 5 is constituted by a main body 5a for manipulation portion and a cover 5b for manipulation portion, both also defining an outer sheath of the manipulation portion; a bending mechanism for performing a remote bending operation (flexing operation) of the curved portion 2b (to be explained hereinafter); and an air/liquid feeding channel for feeding a fluid to a distal end portion of the flexible inserting tube 2. The main body 5a is provided with a manipulating lever (bending operation lever) 5c which is made rotatable for performing the bending operation of the curved portion 2b.

The main body 5a is also provided, at a head portion (proximal portion) thereof, with an ocular portion 6 for enabling an image of a subject to be directly observed. Further, this ocular portion 6 is designed to be detachably connected with a camera (not shown) having a CCD (imaging device) and an image pickup optical system built therein. Therefore, it is possible to observe a subject as a monitor image.

Further, on one side of the main body 5a which is opposite to the other side where the manipulating lever (bending operation lever) 5c is secured, there is mounted a light guide flexible tube (flexible tube for endoscope) 7 in which a light guide 3B (to be explained hereinafter) is introduced. A distal end portion of this light guide flexible tube 7 is connected with a connector 8 which is designed to be connected with a light source (not shown).

The flexible inserting tube 2 is designed to be introduced into a body cavity on the occasion of employing the endoscope. As shown in FIG. 1, this flexible inserting tube 2 comprises a flexible tube 2a which is located on the proximal end side, and a curved portion 2b which is located on the distal end side and enabled to crook or flex. This curved portion 2b is provided, at a distal end thereof, with a fore-end portion 2c, and this fore-end portion 2c is provided, at a distal end thereof, with a foremost-end portion 2d.

As shown in FIG. 2, the flexible inserting tube 2 is provided therein with an image guide 3A, a light guide 3B, a forceps-inserting tube 3C, an air-feeding tube 3D and a liquid-feeding tube 3E. These members are all disposed to extend longitudinally. Further, this flexible inserting tube 2 is formed of a laminate structure consisting of, when mentioned from the inner side thereof, a wire-inserting layer 3a, an inner sheath 3b and an outer sheath 3c.

The image guide 3A is constituted by a plurality of optical fibers which are covered with a protective tube 3d and enabled to act to transmit an image of a subject to the ocular portion 6. These optical fibers are bundled at the opposite ends thereof, i.e., at the ocular portion 6 and the foremost-end portion 2d, by making use of an adhesive, permitting other portions of optical fibers to freely move individually.

As shown in FIG. 3, an objective lens 3F is mounted at the foremost-end portion 2d of flexible inserting tube 2. A distal end (incident end) of the image guide 3A is connected with this objective lens 3F.

This objective lens 3F acts to form an image of a subject at the incident end of the image guide 3A.

The light guide 3B is designed to guide the light from the light source of lighting device (not shown) which is connected with the connector 8 to thereby illuminate a region in front of the foremost-end portion 2d. By doing so, it is possible to obtain a sufficient illuminating light required on the occasion of observing a subject.

This light guide 3B is constituted by a bundle of optical fibers wherein a plurality of optical fibers are covered with a protective tube 3e. These optical fibers are bundled each other at the opposite ends thereof, i.e., at the ocular portion 6 and the foremost-end portion 2d, by making use of an adhesive, permitting other portions of optical fibers to individually move away from others.

In the case of this light guide 3B, if the diameter of each of optical fibers constituting this light guide 3B exceeds the aforementioned upper limit, the bending performance of the optical fibers may be degraded depending on the kind of constituent materials. On the other hand, if the diameter of each of optical fibers is less than the aforementioned lower limit, the light-guiding efficiency of the optical fibers may be degraded occasionally depending on the kind of constituent materials.

The forceps-inserting tube 3C is formed of a hollow structure, thus enabling forceps to be introduced therein. By making use of these forceps, various kinds of operation or treatment can be performed in body cavity in the vicinity of the foremost-end portion 2d of endoscope 1. Incidentally, it is possible to introduce into this forceps-inserting tube 3C various kinds of medical operating instruments and diagnostic instruments other than forceps.

The air-feeding tube 3D and the liquid-feeding tube 3E are both opened at the distal end of flexible inserting tube 2, thereby enabling a fluid to be injected into a body cavity from these opened distal ends or enabling a fluid to be sucked out of a body cavity. For example, by making use of the liquid-feeding tube 3E, washing water or chemical liquid that has been introduced from the air/liquid-feeding channel of the manipulation portion 5 can be injected to a region of body cavity located in the vicinity of the foremost-end portion 2d that has been inserted and retained in the body cavity. Alternatively, a body fluid, etc., existing in the vicinity of this foremost-end portion 2d can be taken up therefrom.

By rotating the manipulating lever (bending operation lever) 5c, the wire 3G can be pulled or loosened. By doing so, the curved portion 2b of flexible inserting tube 2 can be crooked in a predetermined direction.

As shown in FIG. 3, when the curved portion 2b of flexible inserting tube 2 is crooked or when the flexible inserting tube 2 is caused to bend in order to make it follow up the curvature of body cavity, each of the aforementioned members are pulled or caused to move in a predetermined direction in conformity with the crooked direction.

On this occasion, friction is caused to be generated among these members, thus increasing the curving resistance of the flexible inserting tube 2. Because of this, the granular solid lubricant 4 is provided inside the flexible inserting tube 2, i.e., around each of these members, thereby making it possible to minimize the friction among these members and to decrease the curving resistance of the flexible inserting tube 2.

In the case of the endoscope according to this embodiment, the solid lubricant 4 is interposed at interstices between the members such as various kinds of tubes including the protective tube 3d of image guide 3A, the protective tube 3e of light guide 3B, the forceps-inserting tube 3C, the air-feeding tube 3D, the liquid-feeding tube 3E and the wire 3G, and, at the same time, the solid lubricant 4 is interposed at interstices between the optical fibers constituting the image guide 3A and the light guide 3B. The properties and average particle diameter of the solid lubricant 4 may be changed depending on the location (i.e., among these members and among the optical fibers) to be filled with the solid lubricant 4.

As described above, since the solid lubricant 4 which is excellent in lubricity is introduced so as to surround each of optical fibers constituting the optical fiber bundle of the image guide 3A and the optical fiber bundle of the light guide 3B, it is possible to minimize the frictional resistance at the optical fiber-optical fiber interface as well as at the optical fiber-protective tubes 3d, 3e interfaces. As a result, these optical fibers are individually enabled to smoothly move, thus decreasing the flexing resistance of the flexible inserting tube 2. Therefore, it is now possible to suppress, on the occasion of bending the flexible inserting tube 2, the pulling, oppression and buckling against the each of optical fibers. As a result, it is possible to effectively prevent the damage or fracture of the image guide 3A and the optical fiber bundle of the light guide 3B.

The features of the endoscope according to one embodiment of the present invention reside in the composition of the solid lubricant. Namely, the solid lubricant to be employed in the endoscope according to the present invention is selected from those comprising a rice-bran ceramics, or those comprising a rice-bran ceramics, and carbon graphite and/or fluorinated resin.

As for the solid lubricant 4 to be interposed at interstices between these members, it should preferably be selected from those having an average particle diameter of 100 μm. As for the solid lubricant 4 to be interposed in the gaps between the optical fibers, it should preferably be selected from those having an average particle diameter of 1 μm.

Incidentally, sterilization of high-degree using a hydrogen peroxide-based liquid disinfectant is sometimes applied to the endoscope before and after the use thereof. In the case of the conventional endoscope using molybdenum disulfide as a lubricant, the lubricant contained in the inserting tube portion is permitted to react with this liquid disinfectant, resulting in the degradation or corrosion of the lubricant, thus rendering the endoscope incapable of withstanding a long period of use. Whereas, in the case of the endoscope according to one embodiment of the present invention, since the solid lubricant 4 containing rice-bran ceramics is very excellent in chemical resistance, even if the solid lubricant 4 is contacted with a liquid disinfectant, the solid lubricant 4 can be hardly denatured or degraded. Therefore, in the case of the endoscope 1 wherein this solid lubricant 4 is employed, even if the endoscope 1 is kept in an environment where the endoscope 1 is always contacted with chemicals such as a disinfectant, the solid lubricant 4 would not be degraded, thus making it possible to use the endoscope 1 for a long time. As described above, the solid lubricant 4 is not only excellent in lubricity but also in chemical resistance, thus making it possible, due to the aforementioned synergistic effects, to provide the endoscope 1 which is excellent in performance.

Next, the features of the solid lubricant 4 will be explained in detail.

The reasons for employing a solid lubricant containing a rice-bran ceramics, or a solid lubricant containing a rice-bran ceramics, and carbon graphite and/or fluorinated resin are as follows. Namely, by formulating the solid lubricant in these manners, it is possible to obtain a solid lubricant which is more excellent in lubricity and also in resistance to sterilization treatments as compared with a solid lubricant comprising molybdenum disulfide that has been conventionally employed in the endoscope.

Especially, the rice-bran ceramics is advantageous in that it hardly absorbs water so that the excellent lubricity thereof can be maintained for a long time even if the endoscope 1 is subjected, for example, to repeated steam sterilization.

As for the rice-bran ceramics to be included in the solid lubricant to be employed in the endoscope according to one embodiment of the present invention, it is possible to employ, for example, a porous carbonaceous material described in JP-A 10-101453. This porous carbonaceous material can be manufactured by a method comprising the steps of: adding a thermosetting resin and an appropriate quantity of an adhesive paste-containing aqueous solution or of water to brans such as rice bran and other grain bran to form a mixture and kneading the mixture; granulating the kneaded mixture comprising the thermosetting resin and the brans to obtain granules having a predetermined grain size; filling a desired mold with the granules and molding the granules while applying pressure and deaeration to the granules to form a molded product; sintering the molded product released from the mold in an inert gas atmosphere or in a vacuum by increasing the temperature of the molded product up to an ultimate sintering temperature according to a predetermined rate of temperature increase to obtain a carbonized product; and cooling the carbonized product from the ultimate sintering temperature down to ordinary temperature according to a predetermined rate of temperature drop.

This porous carbonaceous material includes relatively flattened voids having clear profile and being dispersed to partially form a sponge-like configuration, wherein most of the voids are encircled densely by carbon atoms which are irregularly flexed to form a continuous or laminar stereostructure.

The porous carbonaceous material that has been sintered at a temperature of not less than 500° C. is characterized by a very low frictional coefficient, so that it is very excellent for use as a lubricant. Further, this porous carbonaceous material is very excellent in heat resistance and cannot be oxidized even in a high-temperature/high-pressure steam atmosphere or in an atmosphere containing hydrogen peroxide or free radicals, thus exhibiting excellent corrosion resistance. Further, this porous carbonaceous material is also very excellent in adhesion thereof to metals and glass.

Because of these reasons, the porous carbonaceous material described in JP-A 10-101453 is very suited for use as a rice bran ceramics to be included in the solid lubricant to be employed in the endoscope of the present invention.

As for specific examples of the rice bran, it is possible to employ RB ceramics (trade name: Sanwa Yushi Co., Ltd.).

As for specific examples of the fluorinated resin, it is possible to employ polytetrafluoroethylene.

In the case of the solid lubricant containing rice-bran ceramics, and carbon graphite and/or fluorinated resin, a mixing ratio of the carbon graphite and/or fluorinated resin to the rice-bran ceramics should preferably be not more than 9 to 1.

With respect to the configuration of the solid lubricant, although there is not any particular limitation, it is more preferable that the solid lubricant is formed of powder. If the solid lubricant is formed of powder, it is possible to enable the solid lubricant to easily enter into a narrow space, thus making the lubricity of built-in member further smoother.

When the solid lubricant is formed of powder, an average particle diameter of the powder may preferably be confined to the range of 0.1 to 150 μm, more preferably 5 to 100 μm though there is not any particular limitation regarding the average particle diameter of the powder. Further, it is also possible to employ a blend containing the powder having an average particle diameter of 5 μm and the powder having an average particle diameter of 100 μm.

Further, the surface of particles of the solid lubricant may be covered with an unsaturated ester monomer containing fluoroaliphatic group or with an unsaturated monosilane monomer, thereby effectively preventing the solid lubricant from being denatured or degraded by a hydrogen peroxide-based liquid disinfectant or by high-temperature/high-pressure steam.

The solid lubricant to be employed in the endoscope according to one embodiment of the present invention may be combined with silicone oil to enable them to exhibit synergistic effects exceeding a total of the effects to be derived from each of these components.

Although the endoscope according to one embodiment of the present invention has been explained with reference to drawings in the foregoing description, the present invention is not limited to this embodiment and hence, the construction of each of the components may be replaced by any optional one having a similar function.

For example, although the above embodiment is directed to an optical endoscope employing an optical fiber bundle as an image guide, the present invention is not limited to such an optical endoscope, but may be applied to an electronic endoscope having a CCD (imaging device) built in a distal end portion of the flexible inserting tube.

Further, although the aforementioned embodiment is directed to an endoscope for medical use, the present invention is not limited to this, but may be applied to an endoscope for industrial use.

EXAMPLES

Next, examples of the present invention as well as comparative examples will be explained to thereby more specifically illustrate the present invention.

Example 1

For the manufacture of the flexible tube of endoscope shown in FIG. 2, a mixture of 80% by weight of rice bran ceramics having an average particle diameter 100 μm, and 20% by weight of polytetrafluoroethylene having an average particle diameter 10 μm was employed as the solid lubricant 4, thereby assembling a bronchial endoscope as shown in FIG. 1.

Example 2

For the manufacture of the flexible tube of endoscope shown in FIG. 2, rice bran ceramics having an average particle diameter 100 μm, and an unsaturated ester monomer having fluoroaliphatic group were employed as the solid lubricant 4, thereby assembling a bronchial endoscope as shown in FIG. 1.

Example 3

For the manufacture of the flexible tube of endoscope shown in FIG. 2, rice bran ceramics having an average particle diameter 100 μm was employed as the solid lubricant 4, thereby assembling a bronchial endoscope as shown in FIG. 1.

Comparative Example 1

For the manufacture of the flexible tube of endoscope shown in FIG. 2, molybdenum disulfide having an average particle diameter 1.5 μm was employed as the solid lubricant 4, thereby assembling a bronchial endoscope as shown in FIG. 1.

Reference Example

For the manufacture of the flexible tube of endoscope shown in FIG. 2, polytetrafluoroethylene having an average particle diameter 10 μm was employed as the solid lubricant 4, thereby assembling a bronchial endoscope as shown in FIG. 1.

(Assessments)

Each of endoscopes of Examples, Comparative Example and Reference Example was assessed as follows.

1) Coverage Property of Protective Tube:

The coverage property of protective tube to the optical fiber bundle on the occasion of manufacturing the endoscope was assessed according to the criterion based on the following four stages.

⊚: Very excellent
○: Excellent
Δ: Somewhat difficult
X: Difficult

2) Resistance to Steam:

As a first test, to each of the endoscopes, autoclave sterilization (high-pressure/high-temperature steam sterilization) was applied 100 times and then, by making use of each of the endoscopes that had undergone the test on bending manipulability after 100 times of the autoclave sterilization, the observation of the interior of body cavity of human phantom was performed. Thereafter, the generation of breakage of optical fibers constituting the optical fiber bundle of the light guide was investigated.

Then, as a second test, to each of the endoscopes, hydrogen peroxide low temperature plasma sterilization was applied 100 times and then, by making use of each of the endoscopes that had undergone the test on bending manipulability after 100 times of the hydrogen peroxide low temperature plasma sterilization, the observation of the interior of body cavity of human phantom was performed. Thereafter, the bending manipulation of the curved portion was repeatedly performed. Then, the generation of breakage of optical fibers constituting the optical fiber bundle of the light guide was investigated.

The results of the first test and the second test were assessed according to the criterion based on the following four stages.
⊚: Breakage of optical fibers was less than 5%
○: Breakage of optical fibers was 5% to less than 20%
Δ: Breakage of optical fibers was 20% to less than 50%
X: Breakage of optical fibers was more than 50%

The results of the assessment are shown in the following Table 1.

TABLE 1

|  | Coverage property | Fist test Resistance to steam | Second test Resistance to peroxide |
|---|---|---|---|
| Example 1 | ○ | ⊚ | ○ |
| Example 2 | ○ | ⊚ | ⊚ |
| Example 3 | ○ | ⊚ | ○ |
| Comparative Example | ○ | X | X |
| Reference Example | ○ | ○ | ○ |

As seen from above Table 1, in the cases of the endoscopes of Examples 1-3, even if they were repeatedly used, the breakage of optical fibers was limited to small numbers and the resistance to steam and hydrogen peroxide was found excellent. Further, in the cases of the endoscopes of Examples 1-3, they exhibited excellent bending manipulability, so that even after the repeated sterilization treatment, this excellent bending manipulability was sustained. Moreover, in the cases of the endoscopes of Examples 1-3, the coverage property of protective tube to the optical fiber bundle on the occasion of manufacturing the endoscope was also found excellent. Whereas, in the case of the endoscopes of Comparative Example, the durability thereof was degraded after the steam sterilization.

Appendix:

1. An endoscope comprising a flexible tube and a protective tube placed in the flexible tube, said protective tube containing a plurality of elongated built-in components including an optical fiber bundle, characterized in that a solid lubricant containing rice-bran ceramics is interposed at interstices between the optical fibers placed in the protective tube and between the protective tube and the flexible tube.

2. An endoscope comprising a flexible tube and a protective tube placed in the flexible tube, said protective tube containing a plurality of elongated built-in components including an optical fiber bundle, characterized in that a solid lubricant containing rice-bran ceramics, and carbon graphite and/or fluorinated resin is interposed at interstices between the optical fibers placed in the protective tube and between the protective tube and the flexible tube.

3. The endoscope according to Appendix No. 1, wherein a mixing ratio of the carbon graphite and/or fluorinated resin to the rice-bran ceramics is not more than 9 to 1.

4. The endoscope according to Appendix No. 1 or 2, wherein the surface of particles of the solid lubricant is covered with an unsaturated ester monomer containing fluoroaliphatic group or an unsaturated monosilane monomer.

5. The endoscope according to any one of Appendix Nos. 1-4, wherein the solid lubricant has an average particle diameter ranging from 0.1 to 150 μm.

6. The endoscope according to any one of Appendix Nos. 1-5, wherein the solid lubricant interposed at interstices between the optical fibers placed in the protective tube has an average particle diameter ranging from 0.1 to 150 μm, and the solid lubricant interposed between the protective tube and the flexible tube has an average particle diameter ranging from 0.1 to 150 μm.

7. The endoscope according to Appendix No. 1 or 2, wherein the rice-bran ceramics is formed of a porous carbonaceous material which is manufactured by a process comprising the steps of: adding a thermosetting resin and an appropriate quantity of an adhesive paste-containing aqueous solution or of water to brans such as rice bran and other grain bran to form a mixture and kneading the mixture; granulating the kneaded mixture of the thermosetting resin and the brans to obtain granules having a predetermined grain size; filling a desired mold with the granules and molding the granules while applying pressure and deaeration to the granules to form a molded product; sintering the molded product released from the mold in an inert gas atmosphere or in a vacuum by increasing the temperature of the molded product up to an ultimate sintering temperature according to a predetermined rate of temperature increase to obtain a carbonized product; and cooling the carbonized product from the ultimate sintering temperature down to ordinary temperature according to a predetermined rate of temperature drop.

8. The endoscope according to Appendix No. 7, wherein the porous carbonaceous material includes relatively flattened voids having clear profile and being dispersed to partially form a sponge-like configuration, wherein most of the voids are encircled densely by carbon atoms which are irregularly flexed to form a continuous or laminar stereostructure.

9. The endoscope according to Appendix No. 8, wherein the porous carbonaceous material is sintered at a temperature of not less than 500° C.

10. The endoscope according to Appendix No. 2, wherein the fluorinated resin is polytetrafluoroethylene.

11. The endoscope according to Appendix No. 1 or 2, wherein the solid lubricant is in a state of powder.

12. The endoscope according to Appendix No. 1 or 2, wherein the elongated built-in components including an optical fiber bundle placed in a protective tube include an image guide or a light guide.

The invention claimed is:

1. An endoscope comprising a flexible tube and a protective tube placed in the flexible tube, said protective tube containing a plurality of elongated built-in components including an optical fiber bundle, characterized in that a solid lubricant containing rice-bran ceramics, and carbon graphite and/or fluorinated resin is interposed at interstices between the optical fibers placed in the protective tube and between the protective tube and the flexible tube, wherein a mixing ratio of the carbon graphite and/or fluorinated resin to the rice-bran ceramics is not more than 9 to 1 by weight.

2. The endoscope according to claim 1, wherein the surface of particles of the solid lubricant is covered with an unsaturated ester monomer containing fluoroaliphatic group or an unsaturated monosilane monomer.

3. The endoscope according to claim 1, wherein the solid lubricant has an average particle diameter ranging from 0.1 to 150 μm.

4. The endoscope according to claim 3, wherein the solid lubricant interposed at interstices between the optical fibers placed in the protective tube has an average particle diameter ranging from 0.1 to 150 μm, and the solid lubricant interposed between the protective tube and the flexible tube has an average particle diameter ranging from 0.1 to 150 μm.

5. The endoscope according to claim 1, wherein the rice-bran ceramics is formed of a porous carbonaceous material which is manufactured by a process comprising adding a thermosetting resin and an appropriate quantity of an adhesive paste-containing aqueous solution or of water to brans such as rice bran and other grain bran to form a mixture and kneading the mixture; granulating the kneaded mixture of the thermosetting resin and the brans to obtain granules having a predetermined grain size; filling a desired mold with the granules and molding the granules while applying pressure and deaeration to the granules to form a molded product; sintering the molded product released from the mold in an inert gas atmosphere or in a vacuum by increasing the temperature of the molded product up to an ultimate sintering temperature according to a predetermined rate of temperature increase to obtain a carbonized product; and cooling the carbonized product from the ultimate sintering temperature down to ordinary temperature according to a predetermined rate of temperature drop.

6. The endoscope according to claim 1, wherein the elongated built-in components including an optical fiber bundle placed in a protective tube include an image guide or a light guide.

* * * * *